United States Patent
Baty et al.

(10) Patent No.: US 10,174,115 B2
(45) Date of Patent: Jan. 8, 2019

(54) ANTI-MGLUR2 CONFORMATIONAL SINGLE DOMAIN ANTIBODIES AND USES THEREOF

(71) Applicants: INSERM (INSTITUT NATIONAL DE LA SANTÉ ET DE LA RECHERCHE MÉDICALE), Paris (FR); UNIVERSITÉ D'AIX MARSEILLE, Marseilles (FR); UNIVERSITE DE MONTPELLIER, Montpellier (FR); CISBIO BIOASSAYS, Codolet (FR); CENTRE NATIONAL DE LA RECHERCHE SCIENTIFIQUE (CNRS), Paris (FR); INSTITUT JEAN PAOLI & IRENE CALMETTES, Marseilles (FR); UNIVERSITÉ PARIS-SUD, Orsay (FR); UNIVERSITÉ DE VERSAILLES SAINT-QUENTIN-EN-YVELINES, Versailles (FR)

(72) Inventors: Daniel Baty, Marseilles (FR); Jean-Philippe Pin, Montpellier (FR); Patrick Chames, Marseilles (FR); Damien Nevoltris, Codolet (FR); Philippe Rondard, Montpellier (FR); Pauline Scholler, Montpellier (FR); Gérard Mathis, Codolet (FR)

(73) Assignees: INSERM (INSTITUT NATIONAL DE LA SANTÉ ET DE LA RECHERCHE MÉDICALE, Paris (FR); UNIVERSITÉ D'AIX MARSEILLE, Marseilles (FR); UNIVERSITE DE MONTPELLIER, Montpellier (FR); CISBIO BIOASSAYS, Codolet (FR); CENTRE NATIONAL DE LA RECHERCHE SCIENTIFIQUE (CNRS), Paris (FR); INSTITUT JEAN PAOLI & IRENE CALMETTES, Marseilles (FR); UNIVERSITÉ PARIS-SUD, Orsay (FR)

( * ) Notice: Subject to any disclaimer, the term of this patent is extended or adjusted under 35 U.S.C. 154(b) by 0 days.

(21) Appl. No.: 15/323,607

(22) PCT Filed: Jul. 3, 2015

(86) PCT No.: PCT/EP2015/065228
§ 371 (c)(1),
(2) Date: Jan. 3, 2017

(87) PCT Pub. No.: WO2016/001417
PCT Pub. Date: Jan. 7, 2016

(65) Prior Publication Data
US 2017/0145098 A1 May 25, 2017

(30) Foreign Application Priority Data

Jul. 4, 2014 (EP) .................................. 14306093

(51) Int. Cl.
C07K 16/28 (2006.01)
A61K 39/395 (2006.01)
A61K 45/06 (2006.01)

(52) U.S. Cl.
CPC ........ C07K 16/286 (2013.01); A61K 39/3955 (2013.01); A61K 45/06 (2013.01); C07K 2317/22 (2013.01); C07K 2317/24 (2013.01); C07K 2317/30 (2013.01); C07K 2317/31 (2013.01); C07K 2317/565 (2013.01); C07K 2317/569 (2013.01); C07K 2317/75 (2013.01)

(58) Field of Classification Search
CPC ............ C07K 16/286; C07K 2317/569; C07K 2317/565; C07K 2317/22; C07K 2317/24; C07K 2317/31; C07K 2317/34; A61K 39/3955; A61K 45/06
See application file for complete search history.

(56) References Cited

U.S. PATENT DOCUMENTS

2015/0320706 A1* 11/2015 Imbimbo ............... A61K 31/05
424/133.1

FOREIGN PATENT DOCUMENTS

EP 0711832 A2 5/1996
WO 2012/175643 A2 12/2012

OTHER PUBLICATIONS

De Genst E et al. Antibody repertoire development in camelids. Developmental & Comparative Immunology, 30:187-198. (Year: 2006).*
Sircar A et al. Analysis and modeling of the variable region of camelid single-domain antibodies. J. Immunology, 186:6357-6367. (Year: 2011).*
Vincke C et al. General strategy to humanize a camelid single-domain antibody and identification of a universal humanized nanobody scaffold. J. Biol. Chem. 284(5):3273-3284. (Year: 2009).*
Zabetakis D et al. Contributions of the complementarity determining regions to the thermal stability of a single-domain antibody. PLoS ONE, 8(10):e77678, 7 pages. (Year: 2013).*
Campo B et al. Characterization of an mGluR2/3 negative allosteric modulator in rodent models of depression. J. Neurogenetics, 25 (4):152-166. (Year: 2011).*

(Continued)

*Primary Examiner* — Kimberly Ballard
(74) *Attorney, Agent, or Firm* — Whitham & Cook, P.C.

(57) ABSTRACT

The present invention relates to anti-metabotropic glutamate receptor subtype 2 (mGluR2) conformational single domain antibodies and uses thereof in particular in the therapeutic and diagnostic field.

18 Claims, 12 Drawing Sheets

Figure 1:
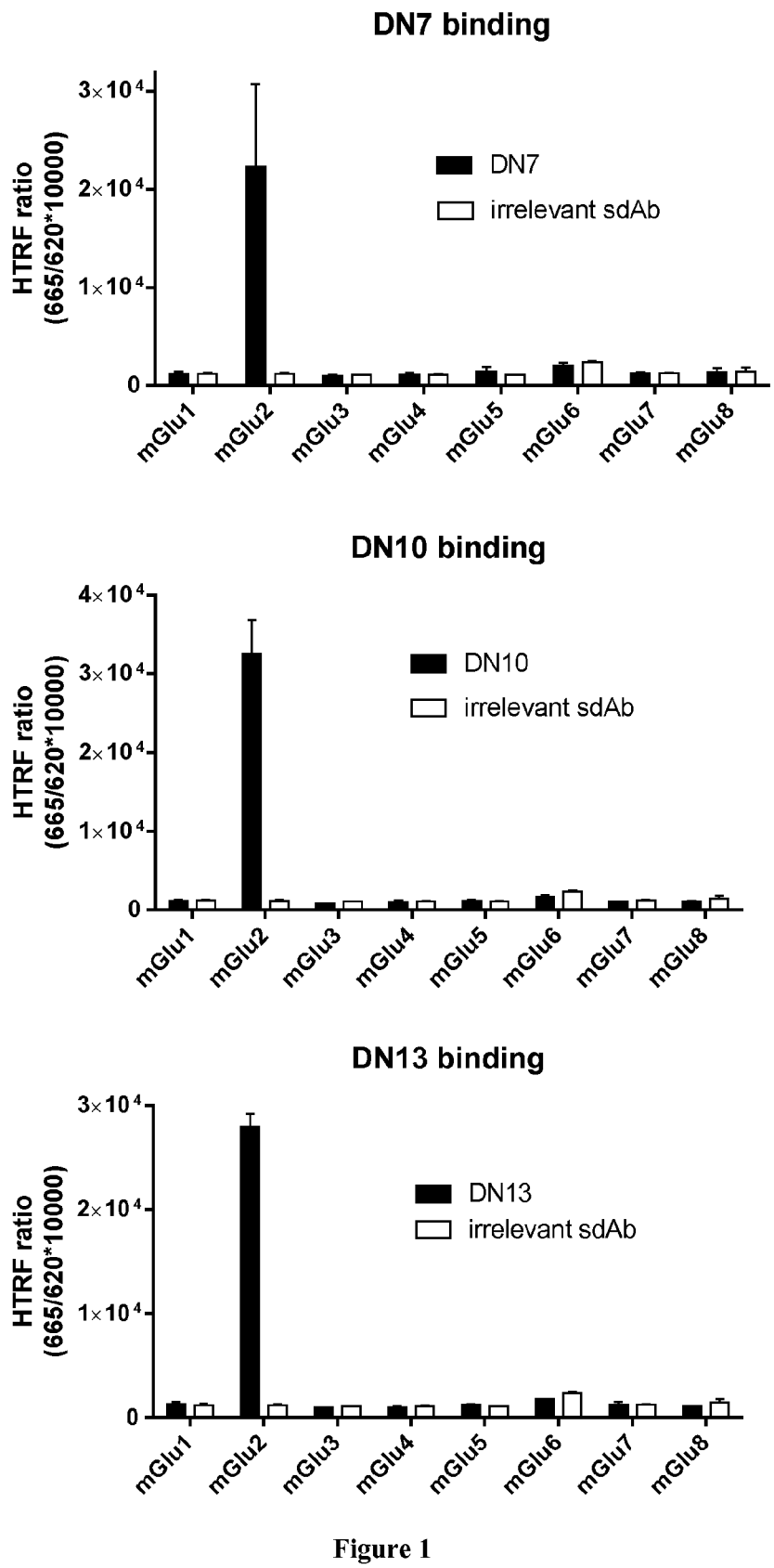

Specification includes a Sequence Listing.

(56) References Cited

OTHER PUBLICATIONS

Hopkins CR. Is there a path forward for mGlu2 positive allosteric modulators for the treatment of schizophrenia? ACS Chem. Neurosci. 4:211-213. (Year: 2013).*

Litman RE et al. AZD8529, a positive allosteric modulator at the mGluR2 receptor, does not improve symptoms in schizophrenia: A proof of principle study. Schizophrenia Res. 172:152-157. (Year: 2016).*

Poisik O et al: "Metabotropic glutamate receptor 2 modulates excitatory synaptic transmission in the rat globus pallidus", Neuropharmacology, Pergamon Press, Oxford, GB, vol. 49, pp. 57-69, Jan. 1, 2005.

Hitoshi Ohishi et al: "Distribution of a metabotropic glutamate receptor, mGluR2, in the central nervous system of the rat and mouse: an immunohistochemical study with a monoclonal antibody", Neuroscience Research, vol. 30, No. 1, pp. 65-82, Jan. 1, 1998.

Andres A Trabanco et al: "mGluR2 positive allosteric modulators: a patent review (2009-present)", Expert Opinion on Therapeutic Patents, vol. 23, No. 5, pp. 629-647, May 1, 2013.

Mark E Fraley: "Positive allosteric modulators of the metabotropic glutamate receptor 2 for the treatment of schizophrenia", Expert Opinion on Therapeutic Patents, Informa Healthcare, GB, vol. 19, No. 9, pp. 1259-1276, Sep. 1, 2009.

E. Doumazane et al: "Illuminating the activation mechanisms and allosteric properties of metabotropic glutamate receptors", Proceedings of the National Academy of Sciences, vol. 110, No. 15, pp. E1416-E1425, Mar. 4, 2013.

* cited by examiner

Hoechst

Donor
(DN1-Tb)

Acceptor (DN13-d2)

Red TR-FRET

ANTI-MGLUR2 CONFORMATIONAL SINGLE DOMAIN ANTIBODIES AND USES THEREOF

FIELD OF THE INVENTION

The present invention relates to anti-mGluR2 conformational single domain antibodies and uses thereof.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptors channels (iGluRs), such as the NMDA, AMPA and kainate receptors which are responsible for fast excitatory transmission. In addition, glutamate activates metabotropic glutamate receptors (mGluRs) which have a more modulatory role that contributes to the fine-tuning of synaptic efficacy. The mGluR2 subtype is negatively coupled to adenylate cyclase via activation of Gai-protein, and its activation leads to inhibition of glutamate release in the synapse. In the central nervous system (CNS), mGluR2 receptors are abundant mainly throughout cortex, thalamic regions, accessory olfactory bulb, hippocampus, amygdala, caudate-putamen and nucleus accumbens.

Activating mGluR2 was shown in clinical trials to be efficacious to treat anxiety disorders. In addition, activating mGluR2 in various animal models was shown to be efficacious, thus representing a potential novel therapeutic approach for the treatment of schizophrenia, epilepsy, addiction/drug dependence, Parkinson's disease, pain, sleep disorders and Huntington's disease.

To date, most of the available pharmacological tools targeting mGluRs are orthosteric ligands which activate several members of the family as they are structural analogs of glutamate. A new avenue for developing selective compounds acting at mGluR2s is to identify compounds that are specific for said subtype, and act through allosteric mechanisms, modulating the receptor by binding to a site different from the highly conserved orthosteric binding domain.

SUMMARY OF THE INVENTION

The present invention relates to anti-mGluR2 conformational single domain antibodies and uses thereof. In particular, the present invention is defined by the claims.

DETAILED DESCRIPTION OF THE INVENTION

In the present invention, the inventors describe the successful selection and the characterization of metabotropic glutamate receptor subtype 2 (mGluR2) conformational single domain antibodies (sdAb). In particular, the inventors isolated 3 different specific anti-mGluR2 clones: DN7, DN10 and DN13. Structure and sequences of said single domain antibodies are depicted in Table A. Interestingly, the binding of all 3 sdAbs was found highly sensitive to ligand stimulation and are able to stabilize the active state of mGluR2 so that the single domain antibodies act as positive allosteric modulators. Accordingly, these antibodies can be very useful for designing new diagnostic and therapeutic tools.

TABLE A sequences of the single domain antibodies or polypeptides of the present invention

| Name | SEQ ID NO: | Sequence |
|---|---|---|
| DN7 CDR1 | 1 | GRTFRPYG |
| DN7 CDR2 | 2 | IIWSLGYT |
| DN7 CDR3 | 3 | AARDRSSSEYDY |
| DN7 | 4 | QVQLVQSGGGYVQAGGSLSVSCAASGRTFRPYGVGWFRQAPGKE REFVAAIIWSLGYTIYADSVKGRFTISRDNAKNTVYLQMNSLKAED TAVYYCAARDRSSSEYDYWGQGTQVTVSS |
| DN10 CDR1 | 5 | GRTDSIYS |
| DN10 CDR2 | 6 | ITWREYT |
| DN10 CDR3 | 7 | ALRPGLRDDLNY |
| DN10 | 8 | EVQLVESGGGVVQPGDSLRLSCVASGRTDSIYSMAWFRQAPGKER EFVAIITWRREYTNYEDSVRGRFTISRDNAKNAVYLQMNKLKPEDT AVYYCALRPGLRDDLNYWGQGTQVTVSS |

TABLE A-continued sequences of the single domain antibodies or polypeptides
of the present invention

| Name | SEQ ID NO: | Sequence |
|---|---|---|
| DN13 CDR1 | 9 | VRFFSINT |
| DN13 CDR2 | 10 | ITSSGST |
| DN13 CDR3 | 11 | HADYKYTTHNTA |
| DN13 | 12 | QVQLVQSGGGLVQAGGSLRLSCAASVRFFSINTMGWYRQAPGKQ RELVADITSSGSTNYADSGKGRFTISRDNAKNTVYLQMNRLKPEDT AVYYCHADYKYTTHNTAWGQGTQVTVSS |

As used herein the term "single domain antibody" has its general meaning in the art and refers to the single heavy chain variable domain of antibodies of the type that can be found in Camelid mammals which are naturally devoid of light chains. Such single domain antibody are also called VHH or "nanobody®". For a general description of single domain antibodies, reference is made to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure : FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the International ImMunoGeneTics information system aminoacid numbering (http://imgt.cines.fr/).

In particular, the present invention relates to an isolated single domain antibody ("DN7 derivative") comprising a CDR1 having least 70% of identity with sequence set forth as SEQ ID NO:1, a CDR2 having at least 70% of identity with sequence set forth as SEQ ID NO:2 and a CDR3 having at least 70% of identity with sequence set forth as SEQ ID NO:3.

In particular, the present invention relates to an isolated single domain antibody ("DN10 derivative") comprising a CDR1 having least 70% of identity with sequence set forth as SEQ ID NO:5, a CDR2 having at least 70% of identity with sequence set forth as SEQ ID NO:6 and a CDR3 having at least 70% of identity with sequence set forth as SEQ ID NO:7.

In particular, the present invention relates to an isolated single domain antibody ("DN13 derivative") comprising a CDR1 having least 70% of identity with sequence set forth as SEQ ID NO:9, a CDR2 having at least 70% of identity with sequence set forth as SEQ ID NO:10 and a CDR3 having at least 70% of identity with sequence set forth as SEQ ID NO:11.

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence. Amino acid sequence identity is typically determined using a suitable sequence alignment algorithm and default parameters, such as BLAST P (Karlin and Altschul, 1990).

In some embodiments the isolated single domain antibody (DN7 derivative) according to the invention comprises a CDR1 having a sequence set forth as SEQ ID NO: 1, a CDR2 having a sequence set forth as SEQ ID NO:2 and a CDR3 having a sequence set forth as SEQ ID NO:3.

In some embodiments the isolated single domain antibody (DN10 derivative) according to the invention comprises a CDR1 having a sequence set forth as SEQ ID NO:5, a CDR2 having a sequence set forth as SEQ ID NO:6 and a CDR3 having a sequence set forth as SEQ ID NO:7.

In some embodiments the isolated single domain antibody (DN13 derivative) according to the invention comprises a CDR1 having a sequence set forth as SEQ ID NO:9, a CDR2 having a sequence set forth as SEQ ID NO:10 and a CDR3 having a sequence set forth as SEQ ID NO:11.

In some embodiments, the isolated single domain antibody according to the invention has the sequence set forth as SEQ ID NO:4 ("DN7").

In some embodiments, the isolated single domain antibody according to the invention has the sequence set forth as SEQ ID NO:8 ("DN10").

In some embodiments, the isolated single domain antibody according to the invention has the sequence set forth as SEQ ID NO:12. ("DN13").

In some embodiments, the single domain antibody is a "humanized" single domain antibody. As used herein the term "humanized" refers to a single domain antibody of the invention wherein an amino acid sequence that corresponds to the amino acid sequence of a naturally occurring VHH domain has been "humanized", i.e. by replacing one or more amino acid residues in the amino acid sequence of said naturally occurring VHH sequence (and in particular in the framework sequences) by one or more of the amino acid residues that occur at the corresponding position(s) in a VH domain from a conventional chain antibody from a human being. Methods for humanizing single domain antibodies are well known in the art. Typically, the humanizing substitutions should be chosen such that the resulting humanized single domain antibodies still retain the favourable properties of single domain antibodies of the invention. The one skilled in the art is able to determine and select suitable humanizing substitutions or suitable combinations of humanizing substitutions. For example, the single domain antibodies of the invention may be suitably humanized at any framework residue provided that the single domain antibodies remain soluble and do not significantly loss their affinity for mGluR2.

A further aspect of the invention refers to a polypeptide comprising at least one single domain antibody of the invention.

Typically, the polypeptide of the invention comprises a single domain antibody of the invention, which is fused at its N terminal end, at its C terminal end, or both at its N terminal end and at its C terminal end to at least one further amino acid sequence, i.e. so as to provide a fusion protein. According to the invention the polypeptides that comprise a sole single domain antibody are referred to herein as "monovalent" polypeptides. Polypeptides that comprise or essentially consist of two or more single domain antibodies according to the invention are referred to herein as "multivalent" polypeptides. In some embodiments, the polypeptide comprises at least one single domain antibody of the invention and at least one other binding domain (e.g. directed against another epitope, antigen, target, protein or polypeptide), which is typically also a single domain antibody. Such a polypeptide is referred to herein as "multispecific" polypeptide; in opposition to a polypeptide comprising the same single domain antibodies ("monospecific" polypeptide).

Thus, in some embodiments, the polypeptide of the invention may also provide at least one further binding domain directed against any desired protein, polypeptide, antigen, antigenic determinant or epitope. Said binding domain is directed against the same protein, polypeptide, antigen, antigenic determinant or epitope for which the single domain antibody of the invention is directed against, or may be directed against a different protein, polypeptide, antigen, antigenic determinant or epitope from the single domain antibody of the invention.

A "bispecific" polypeptide of the invention is a polypeptide that comprises at least one single domain antibody directed against a first antigen (i.e. mGluR2) and at least one further binding domain directed against a second antigen (i.e. different from mGluR2), whereas a "trispecific" polypeptide of the invention is a polypeptide that comprises at least one single domain antibody directed against a first antigen (i.e. mGluR2), at least one further binding domain directed against a second antigen (i.e. different from mGluR2) and at least one further binding domain directed against a third antigen (i.e. different from both i.e. first and second antigen); etc.

In some embodiments, the further binding domain is directed against a serum protein so that the half-life of the single domain antibody is increased. Typically, said serum protein is albumin.

In some embodiments, the further binding domain is directed against a receptor on the vascular endothelium of the blood-brain barrier so that the single domain antibodies of the present invention would cross the blood-brain barrier. The targeted receptors include transferrin receptor, insulin receptor, IGF-I and IGF-II receptors, among others. In a particular embodiment, the further binding domain is directed against transferrin. Transferrin receptor is selectively enriched on the endothelium of the brain microvascular endothelium of a variety of mammals, including humans, and is the primary pathway for iron to enter the brain. Iron-loaded transferrin, an 80 Kd glycoprotein, the principal iron transport protein in the circulation, undergoes transcytosis through the blood-brain barrier via the transferrin receptor. The structure and function of the transferrin receptor have been described in Seligman, Prog. Hematol. 13:131-147 (1983), which is incorporated by reference herein.

Typically, the one or more further binding domain may comprise one or more parts, fragments or domains of conventional chain antibodies (and in particular human antibodies) and/or of heavy chain antibodies. For example, a single domain antibody of the invention may be linked to a conventional (typically human) VH or VL optionally via a linker sequence.

In some embodiments, the polypeptides comprise a single domain antibody of the invention that is linked to an immunoglobulin domain. For example the polypeptides comprise a single domain antibody of the invention that is linked to an Fc portion (such as a human Fc). Said Fc portion may be useful for increasing the half-life and even the production of the single domain antibody of the invention. For example the Fc portion can bind to serum proteins and thus increases the half-life on the single domain antibody. In some embodiments, at least one single domain antibody may also be linked to one or more (typically human) CH1, and/or CH2 and/or CH3 domains, optionally via a linker sequence. For instance, a single domain antibody linked to a suitable CH1 domain could for example be used—together with suitable light chains—to generate antibody fragments/structures analogous to conventional Fab fragments or F(ab')2 fragments, but in which one or (in case of an F(ab')2 fragment) both of the conventional VH domains have been replaced by a single domain antibody of the invention. In some embodiments, one or more single domain antibodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more CH2 and/or CH3 domains of an antibody, such as from a heavy chain antibody and more typically from a conventional human chain antibody; and/or may form and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid VHH domain or a humanized derivative thereof (i.e. a single domain antibody), in which the Camelidae CH2 and/or CH3 domain have been replaced by human CH2 and CH3 domains, so as to provide an immunoglobulin that consists of 2 heavy chains each comprising a single domain antibody and human CH2 and CH3 domains (but no CH1 domain), which immunoglobulin has the effector function provided by the CH2 and CH3 domains and which immunoglobulin can function without the presence of any light chains.

In some embodiment, the polypeptide is as described in WO2006064136. In particular the polypeptide may consist of i) a first fusion protein wherein the CL constant domain of an antibody is fused by its N-terminal end to the C-terminal end to a single domain antibody according to the invention (i.e. a single antibody directed against mGluR2) and ii) a second fusion protein wherein the CH1 constant domain of an antibody is fused by its N-terminal end to the C-terminal end of a single domain antibody directed against an antigen different from mGluR2.

In some embodiments, the polypeptide is a biparatopic polypeptide. As used herein, the term "biparatopic" polypeptide means a polypeptide comprising a single domain antibody and a second single domain antibody as herein defined, wherein these two single domain antibodies are capable of binding to two different epitopes of one antigen (e.g. mGluR2), which epitopes are not normally bound at the same time by one monospecific immunoglobulin, such as e.g. a conventional antibody or one single domain antibody.

In some embodiments, the biparatopic polypeptide of the present invention comprises a DN7 derivative as defined above and a DN10 derivative as defined above.

In some embodiments, the biparatopic polypeptide of the present invention comprises a DN10 derivative as defined above and a DN13 derivative as defined above.

In some embodiments, the biparatopic polypeptide of the present invention comprises a DN7 derivative as defined above and a DN13 derivative as defined above.

In some embodiments, the two single domain antibodies of the biparatopic polypeptide of the present invention can be linked to each other directly (i.e. without use of a linker) or via a linker. The linker is typically a linker peptide and will, according to the invention, be selected so as to allow binding of the two single domain antibodies to each of their at least two different epitopes of mGluR2. Suitable linkers inter alia depend on the epitopes and, specifically, the distance between the epitopes on mGluR2 to which the single domain antibodies bind, and will be clear to the skilled person based on the disclosure herein, optionally after some limited degree of routine experimentation. Also, the two single domain antibodies that bind to mGluR2 may also be linked to each other via a third single domain antibody (in which the two single domain antibodies may be linked directly to the third domain antibody or via suitable linkers). Such a third single domain antibody may for example be a single domain antibody that provides an increased half-life. For example, the latter single domain antibody may be a single domain antibody that is capable of binding to a (human) serum protein such as (human) serum albumin or (human) transferrin, as further described herein. In some embodiments, two or more single domain antibodies that bind to mGluR2 are linked in series (either directly or via a suitable linker) and the third (single) single domain antibody (which may provide for increased half-life, as described above) is connected directly or via a linker to one of these two or more aforementioned single domain antibodies. Suitable linkers are described herein in connection with specific polypeptides of the invention and may—for example and without limitation—comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the anti-mGluR2 polypeptide of the invention is administered. One useful group of linker sequences are linkers derived from the hinge region of heavy chain antibodies as described in WO 96/34103 and WO 94/04678. Other examples are poly-alanine linker sequences such as Ala-Ala-Ala. Further preferred examples of linker sequences are Gly/Ser linkers of different length including (gly4ser)3, (gly4ser)4, (gly4ser), (gly3ser), gly3, and (gly3ser2)3.

```
                                          SEQ ID NO: 13
(GGGGS GGGGS GGGGS)

SEQ ID NO: 14
(GGGGS GGGGS GGGGS GGGGS)

SEQ ID NO: 15
(GGGGS)

SEQ ID NO: 16
(GGS)

SEQ ID NO: 17
(GGG)

SEQ ID NO: 18
(GGGSS GGGSS GGGSS)
```

In some embodiments, it is contemplated that the polypeptides of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications. Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa). In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the polypeptide of the invention described herein for therapeutic delivery.

According to the invention, the single domain antibodies and polypeptides of the invention may be produced by conventional automated peptide synthesis methods or by recombinant expression. General principles for designing and making proteins are well known to those of skill in the art.

The single domain antibodies and polypeptides of the invention may be synthesized in solution or on a solid support in accordance with conventional techniques. Various automatic synthesizers are commercially available and can be used in accordance with known protocols as described in Stewart and Young; Tam et al., 1983; Merrifield, 1986 and Barany and Merrifield, Gross and Meienhofer, 1979. The single domain antibodies and polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the single domain antibodies and polypeptides of the invention, it would be necessary to employ vectors comprising polynucleotide molecules for encoding the single domain antibodies and polypeptides of the invention. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding domains, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence.

A further aspect of the present invention relates to an isolated single domain antibody as positive allosteric modulators of the metabotropic glutamate receptor subtype 2 ("mGluR2") and which are useful for the treatment or prevention of neurological and psychiatric disorders associated with glutamate dysfunction and diseases in which the mGluR2 subtype of metabotropic receptors is involved.

The single domain antibodies or polypeptides of the present invention are positive allosteric modulators of metabotropic glutamate receptors, in particular they are positive allosteric modulators of mGluR2. The single domain antibodies or polypeptides of the present invention do not appear to bind to the glutamate recognition site, the orthosteric ligand site, but instead to an allosteric site within the extracellular domain of the receptor. In the presence of glutamate or an agonist of mGluR2, the single domain antibodies or polypeptides of the present invention increase the mGluR2 response. The single domain antibodies or polypeptides of the present invention provided in this invention are expected to have their effect at mGluR2 by virtue of their ability to increase the response of such receptors to glutamate or mGluR2 agonists, enhancing the response generated by the receptor.

Hence, the present invention relates to a single domain antibody or polypeptide of the present invention for use as a medicament.

The present invention also relates to a single domain antibody or polypeptide of the present invention for use in the treatment or prevention, in particular treatment, of a disease or a condition in a mammal, including a human, the treatment of which is affected or facilitated by the neuromodulatory effect of allosteric modulators of mGluR2, in particular positive allosteric modulators thereof.

As used herein, the terms "treating" or "treatment" or "alleviation" refers to therapeutic treatment, wherein the object is to prevent or slow down (lessen) the targeted disease. A subject is successfully "treated" for a particular disease, if after receiving a therapeutic amount of the single domain antibody according to the invention, the subject shows observable and/or measurable reduction in or absence of one or more signs and symptoms of said disease. In a particular embodiment the treatment is a prophylactic treatment. The term "prophylactic treatment" as used herein, refers to any medical or public health procedure whose purpose is to prevent a disease. As used herein, the terms "prevent", "prevention" and "preventing" refer to the reduction in the risk of acquiring or developing a given condition, or the reduction or inhibition of the recurrence or said condition in a subject who is not ill, but who has been or may be near a subject with the disease. It is also to be appreciated that the various modes of treatment or prevention of medical conditions as described are intended to mean "substantial," which includes total but also less than total treatment or prevention, and wherein some biologically or medically relevant result is achieved.

In some embodiments, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In some embodiments, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

In some embodiments, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

In some embodiments, the central nervous system disorder is a psychotic disorder selected from the group of schizophrenia, delusional disorder, schizoaffective disorder, schizophreniform disorder and substance-induced psychotic disorder In some embodiments, the central nervous system disorder is a personality disorder selected from the group of obsessive-compulsive personality disorder and schizoid, schizotypal disorder.

In some embodiments, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

In some embodiments, the central nervous system disorder is an eating disorder selected from the group of anorexia nervosa and bulimia nervosa.

In some embodiments, the central nervous system disorder is a mood disorder selected from the group of bipolar disorders (I & II), cyclothymic disorder, depression, dysthymic disorder, major depressive disorder and substance-induced mood disorder.

In some embodiments, the central nervous system disorder is migraine.

In some embodiments, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

In some embodiments, the central nervous system disorder is attention-deficit/hyperactivity disorder.

In some embodiments, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of anxiety, schizophrenia, migraine, depression, and epilepsy are of particular importance. At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses. Because such positive allosteric modulators of mGluR2, including single domain antibodies or polypeptides of the present invention, enhance the response of mGluR2 to glutamate, it is an advantage that the present methods utilize endogenous glutamate.

Because positive allosteric modulators of mGluR2, including single domain antibodies or polypeptides of the present invention, enhance the response of mGluR2 to agonists, it is understood that the present invention extends to the treatment of neurological and psychiatric disorders associated with glutamate dysfunction by administering a therapeutically effective amount of a positive allosteric modulator of mGluR2, including single domain antibodies or polypeptides of the present invention, in combination with an mGluR2 agonist. Positive allosteric modulators of mGluRs have emerged recently as novel pharmacological entities offering this attractive alternative. Various compounds have been described as mGluR2 positive allosteric modulators. WO2004/092135 (NPS & Astra Zeneca), WO2004/018386, WO2006/014918 and WO2006/015158 (Merck), WO2001/56990 (Eli Lilly) and WO2006/030032 and WO2007/104783 (Addex & Janssen Pharmaceutica) describe respectively phenyl sulfonamide, acetophenone, indanone, pyridylmethyl sulfonamide and pyridinone derivatives as mGluR2 positive allosteric modulators. None of the specifically disclosed compounds therein are structurally related to the single domain antibodies or polypeptides of the present invention. In some embodiments, the single domain antibody of the present invention is used in combination with a compound selected from the group consisting of ADX-71149, G S K1331258, Imidazo [1,2-a] pyridine s, 3-Aryl-5-phenoxymethyl-1,3-oxazolidin-2-ones, 3-(Imidazolyl methyl)-3-aza-bicyclo [3.1.0]hexan-6-yl) methyl ethers, BINA, and LY-487,379.

The single domain antibodies or polypeptides of the present invention may be utilized in combination with one or more other drugs in the treatment, prevention, control, amelioration, or reduction of risk of diseases or conditions for which single domain antibodies or polypeptides of the present invention or the other drugs may have utility, where the combination of the drugs together are safer or more effective than either drug alone.

According to the invention single domain antibody of the invention or the polypeptide of the invention is administered to the patient with a therapeutically effective amount. By a "therapeutically effective amount" is meant a sufficient amount of the single domain antibody of the invention or the polypeptide of the invention to treat the disease (e.g. central nervous system disorder) at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular patient will depend upon a variety of factors including the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the patient to be treated. A medicament typically contains from about 0.01 mg to about 500 mg of the active ingredient, typically from 1 mg to about 100 mg of the active ingredient. A therapeutically effective amount of the drug is ordinarily supplied at a dosage level from 0.0002 mg/kg to about 20 mg/kg of body weight per day, especially from about 0.001 mg/kg to 7 mg/kg of body weight per day.

The single domain antibodies and polypeptides of the invention or the polypeptide of the present may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropyl cellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

In a further aspect of the present invention, the single domain antibodies of the present invention are used to detect the activation of the mGluR2. For example, said detection is performed by a TR-FRET method as described in WO2010125314. This method is based on the use of two antibodies labelled with a fluorophore donor or acceptor compatible with TR-FRET measurement. It can be either the same single domain antibody specific of the active conformation, or two different antibodies, such as two single domain antibodies specific of the active conformation, or one antibody specific of the active conformation and the other one not specific of the active conformation. Accordingly the present invention provides a method of detecting the activation of mGluR2 in a sample comprising the steps of i) contacting the sample with a single domain antibody or polypeptide of the present invention, ii) and detecting the binding of said single domain antibody or polypeptide to said sample wherein said detection is indicative of the activation of mGluR2. Typically, the sample comprises cells that express naturally or artificially mGluR2. For example said cells are cells that are transformed with a nucleic acid molecule encoding for mGluR2 or cells having an endogenous expression of mGluR2 (e.g. neurons).

Accordingly, in some embodiments, the single domain antibody or polypeptide of the present invention can be conjugated with a detectable label to form an anti-mGluR2 immuno conjugate. Suitable detectable labels include, for example, a radioisotope, a fluorescent label, a chemiluminescent label, an enzyme label, a bio luminescent label or colloidal gold. Methods of making and detecting such detectably-labeled immunoconjugates are well-known to those of ordinary skill in the art, and are described in more detail below. For instance, the detectable label can be a radioisotope that is detected by autoradiography. Isotopes that are particularly useful for the purpose of the present invention are $^3$H, $^{125}$I, $^{131}$I, $^{35}$S and $^{14}$C. Anti-mGluR2 immunoconjugates can also be labeled with a fluorescent compound. The presence of a fluorescently-labeled single domain antibody or polypeptide of the present invention is determined by exposing the immuno conjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine and Alexa Fluor dyes. Alternatively, anti-mGluR2 immunoconjugates can be detectably labeled by coupling a single domain antibody or polypeptide of the present invention to a chemiluminescent compound. The presence of the chemiluminescent-tagged immuno conjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester. Similarly, a bio luminescent compound can be used to label anti-mGluR2 immunoconjugates of the present invention. Bio luminescence is a type of chemiluminescence found in biological systems in which a catalytic protein increases the efficiency of the chemiluminescent reaction. The presence of a bio luminescent protein is determined by detecting the presence of luminescence. Bio luminescent compounds that are useful for labeling include luciferin, luciferase and aequorin. Alternatively, anti-mGluR2 immunoconjugates can be detectably labeled by linking an anti-mGluR2 single domain antibody or polypeptide of the present invention to an enzyme. When the anti-mGluR2-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase. Those of skill in the art will know of other suitable labels which can be employed in accordance with the present invention. The binding of marker moieties to anti-mGluR2 single domain antibodies or polypeptides of the present invention can be accomplished using standard techniques known to the art. Typical methodology in this regard is described by Kennedy et al., Clin. Chim. Acta 70:1, 1976; Schurs et al., Clin. Chim. Acta 81:1, 1977; Shih et al., Int'U. Cancer 46:1101, 1990; Stein et al, Cancer Res. 50:1330, 1990; and Coligan, supra. Moreover, the convenience and versatility of immunochemical detection can be enhanced by using anti-mGluR2 single domain antibodies or polypeptides of the present invention that have been conjugated with avidin, streptavidin, and biotin. {See, e.g., Wilchek et al. (eds.), "Avidin-Biotin Technology," Methods In Enzymology (Vol. 184) (Academic Press 1990); Bayer et al., "Immunochemical Applications of Avidin-Biotin Technology," in Methods In Molecular Biology (Vol. 10) 149-162 (Manson, ed., The Humana Press, Inc. 1992).)

The invention will be further illustrated by the following figures and examples. However, these examples and figures should not be interpreted in any way as limiting the scope of the present invention.

FIGURES

FIG. 1: the single domain antibodies are specific for the mGlu2 receptor over the 8 mGluR subtypes. HTRF signal measured on HEK293 cells expressing the indicated mGlu receptor fused at the N-terminus with a SNAP-tag labeled with Lumi4-Tb, in presence of 100 nM of DN7/DN10/DN13 fused at the C-terminus with a cMyc-tag and 200 nM of anti-cMyc antibody coupled to d2 fluorophores.

Figure 2:
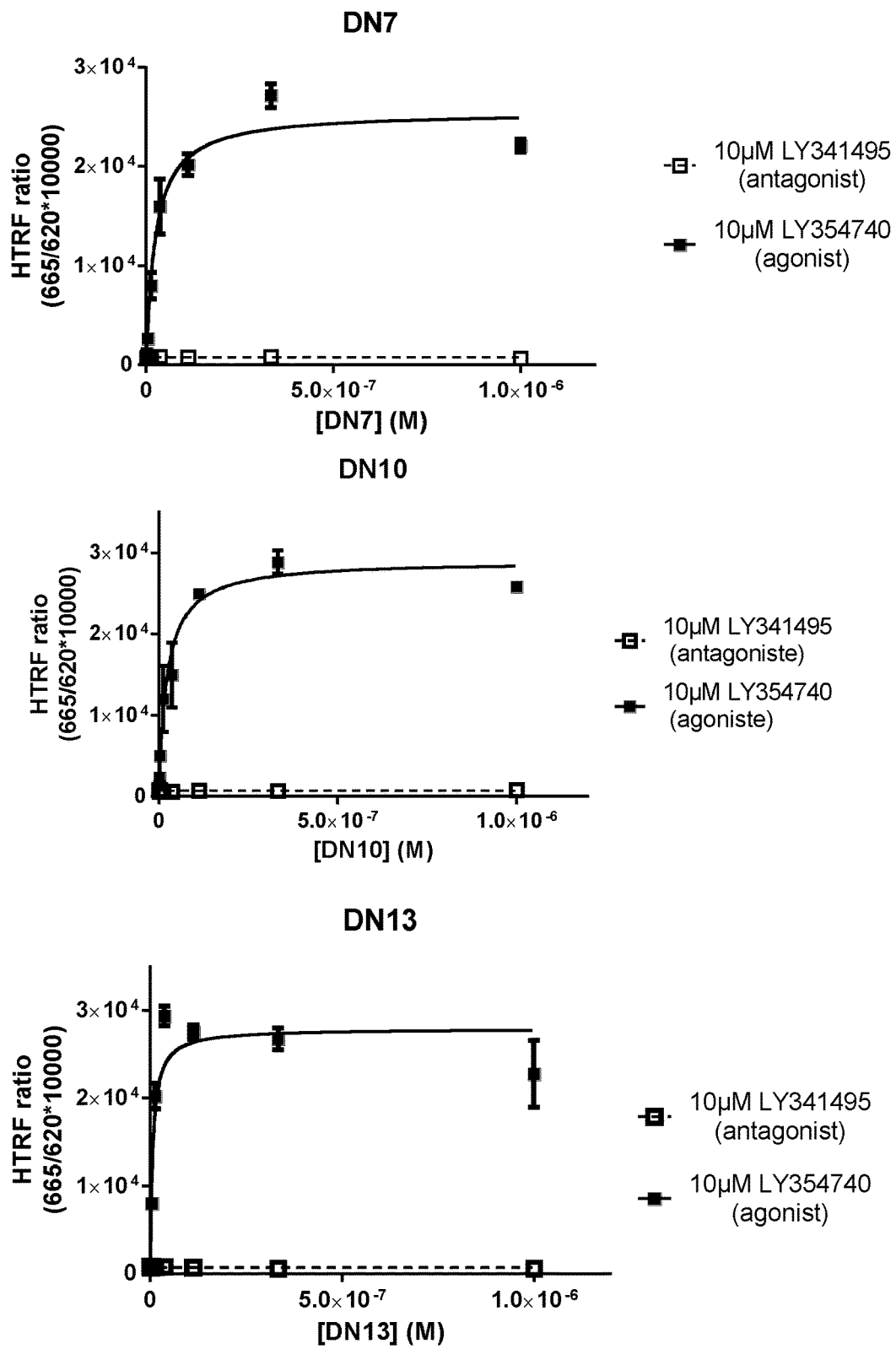

FIG. 2: the single domain antibodies are specific for the active conformation of mGlu2. HTRF signal measured on HEK293 cells expressing the SNAP-tagged mGlu2 receptor labeled with Lumi4-Tb, in the presence of 100 nM of cMyc-tagged DN7/DN10/DN13, 200 nM of anti-cMyc antibody coupled to d2 fluorophores and the indicated mGlu2 ligands.

Figure 3:
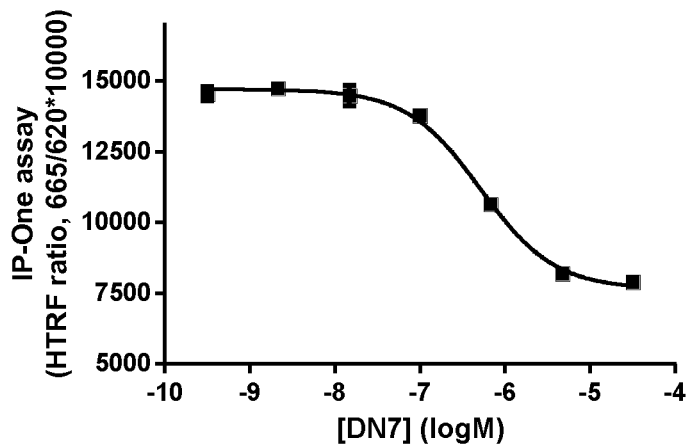
Figure 3:
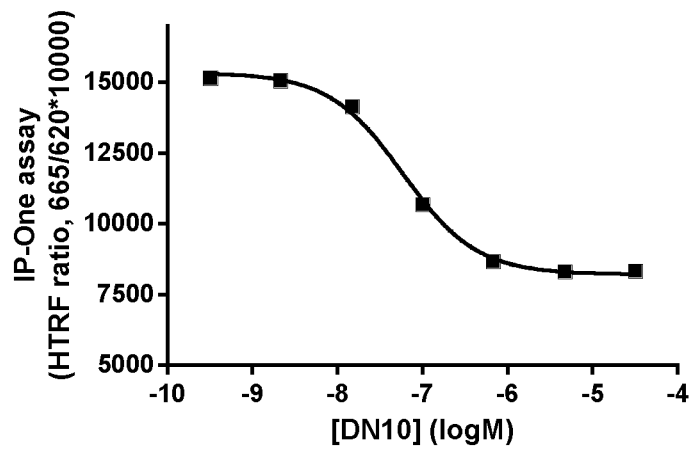
Figure 3:
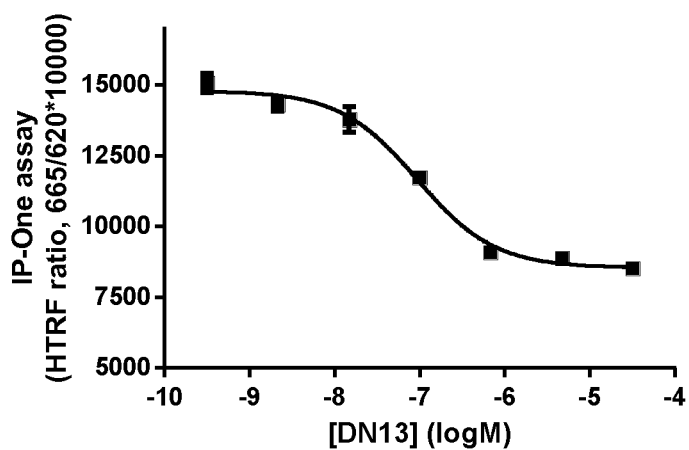

FIG. 3: the single domain antibodies activate mGlu2 in HEK293 transfected cells. inositol phosphate accumulation induced by the indicated concentrations of DN7/DN10/DN13 on HEK293 cells expressing mGlu2 and a chimeric G protein enabling the coupling of mGlu2 to the Gq pathway, measured with the IP-One assay as previously described (Degorce F, Card A, Soh S, Trinquet E, Knapik GP, Xie B. HTRF: A technology tailored for drug discovery—a review of theoretical aspects and recent applications. Curr Chem Genomics. 2009 May 28; 3:22-32.). Briefly, the inositol phosphate produced through G protein activation by mGlu2 competes with an acceptor labeled version of itself for binding to a donor labeled antibody, decreasing the possible FRET signal. Thus, the normalized FRET signal (HTRF ratio) decreases as more inositol phosphate is produced.

Figure 4A:
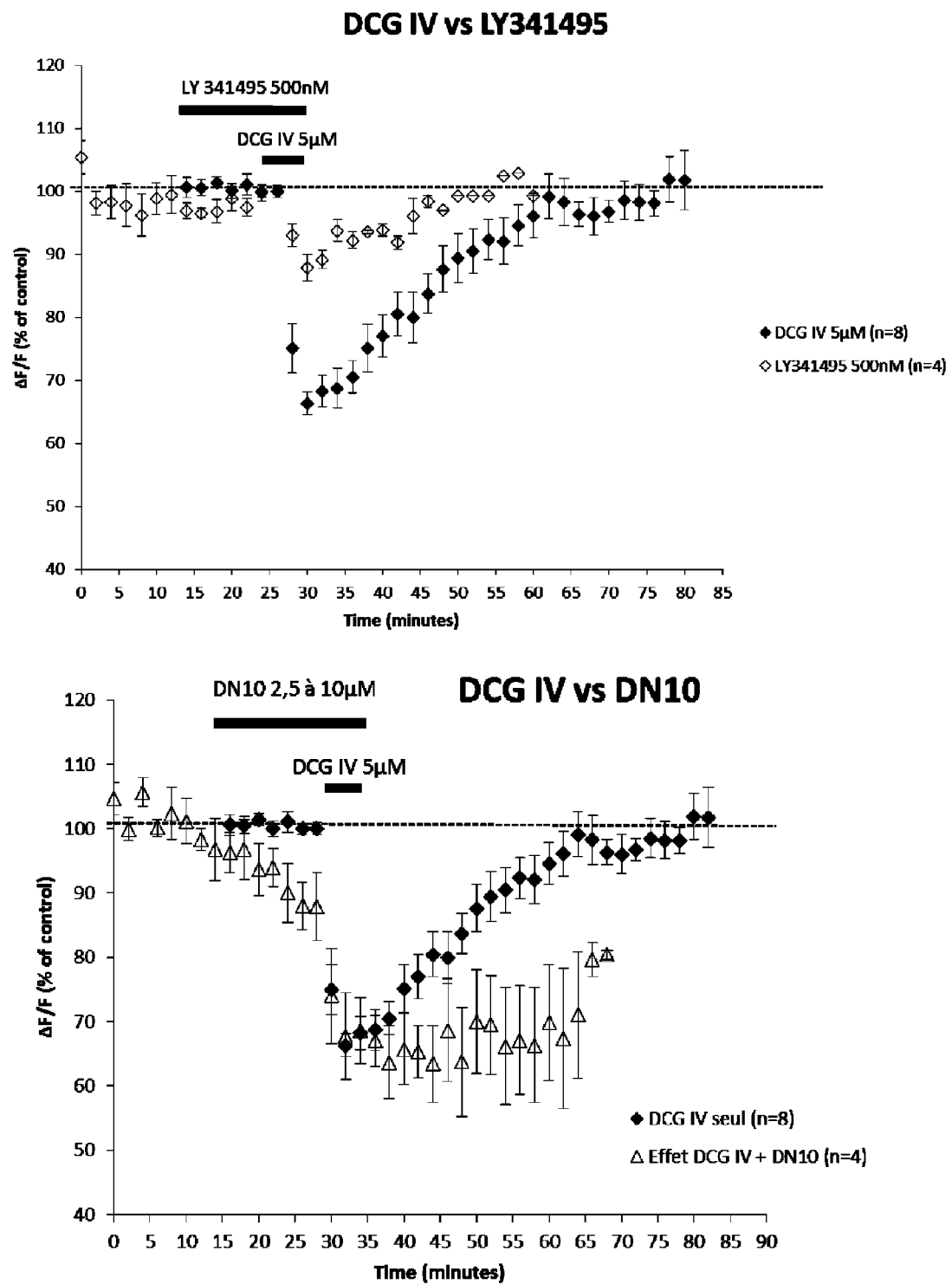
Figure 4B:
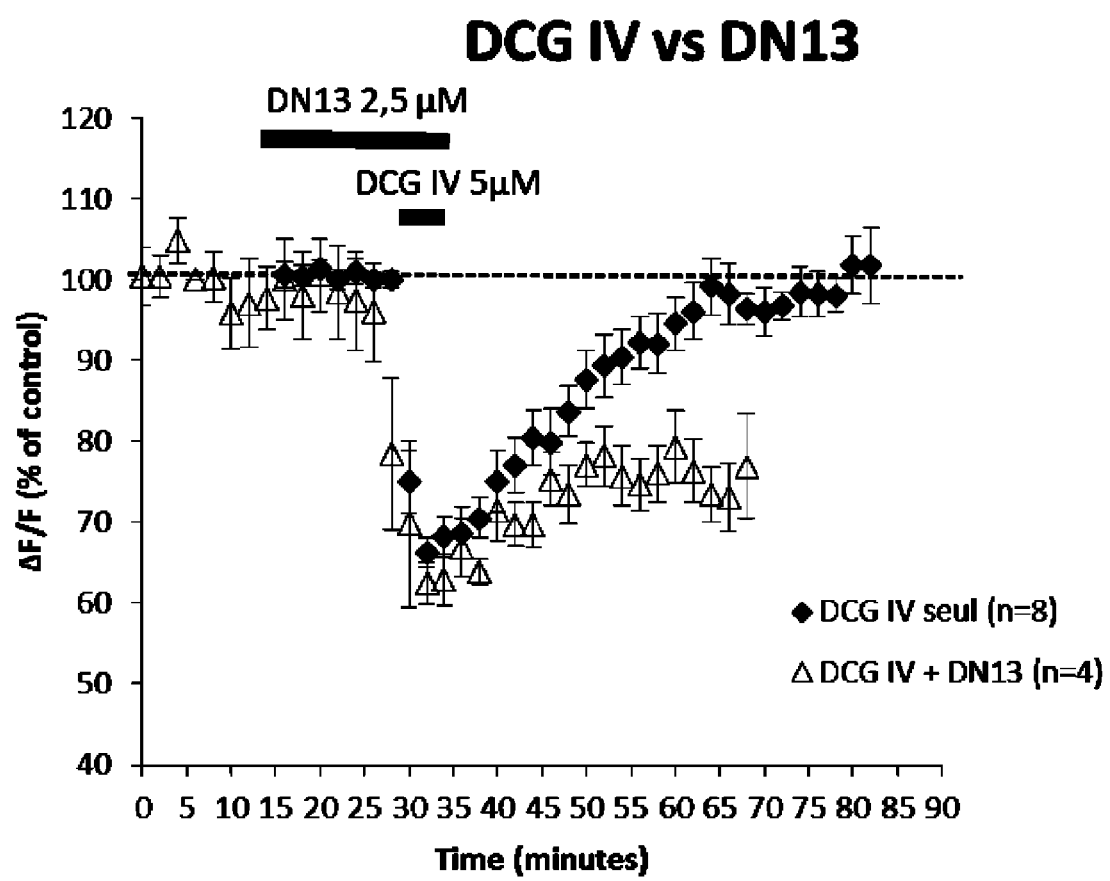

FIGS. 4A and B: the single domain antibodies prevent the dissociation of the agonist in rat hippocampal slices. Effects of DN10/DN13 or the indicated mGlu2 ligand (the agonist DCG-IV or the antagonist LY341495) on presynaptic evoked calcium transients in response to 100-Hz trains in mossy fiber spines loaded with the calcium-sensing dye Magnesium Green-AM in 300 μm thick hippocampal slices from 21-to-25-day-old rats (Regehr & Tank, 1991; Regehr & Atluri, 1995).

Figure 5:
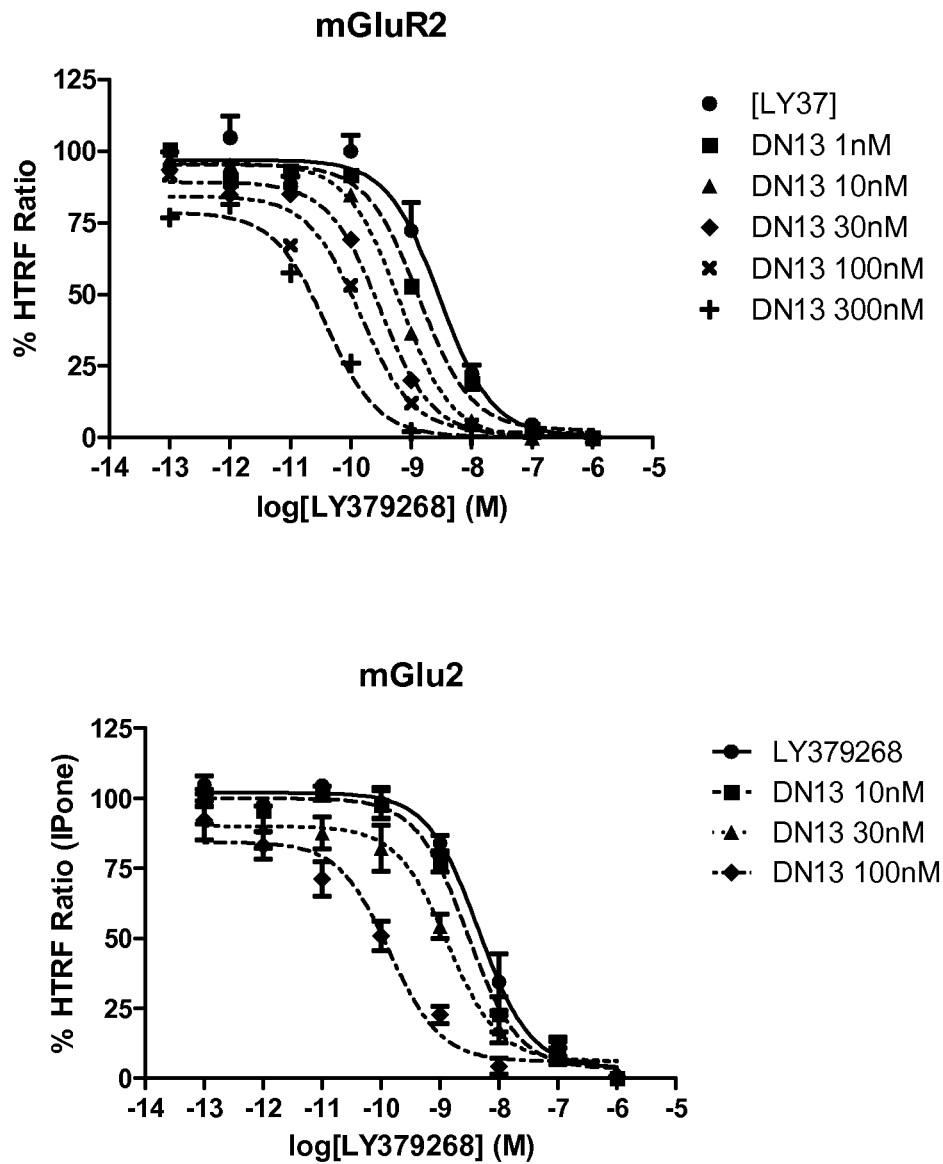

FIG. 5: DN13 is a positive allosteric modulator of mGlu2R. A) Effect of increasing concentrations of DN13 on the effect of the mGlu2R agonist LY379268 on the mGlu2R bio sensor. HTRF signals were measured on the snap-tagged version of mGlu2R. High HTRF represent the inactive form of the receptor, while low HTRF is representative of the active form of the receptor (Doumazane et al., PNAS 2012). B) Effect of increasing concentrations of DN13 on the effect of the mGlu2R agonist LY379268 on the mGlu2R coupling to G proteins. HTRF signals were measured using the IP-One kit from CisBio. High HTRF represents low production of the second messenger IP1, while low HTRF is representative of high concentration of IP1.

Figure 6:
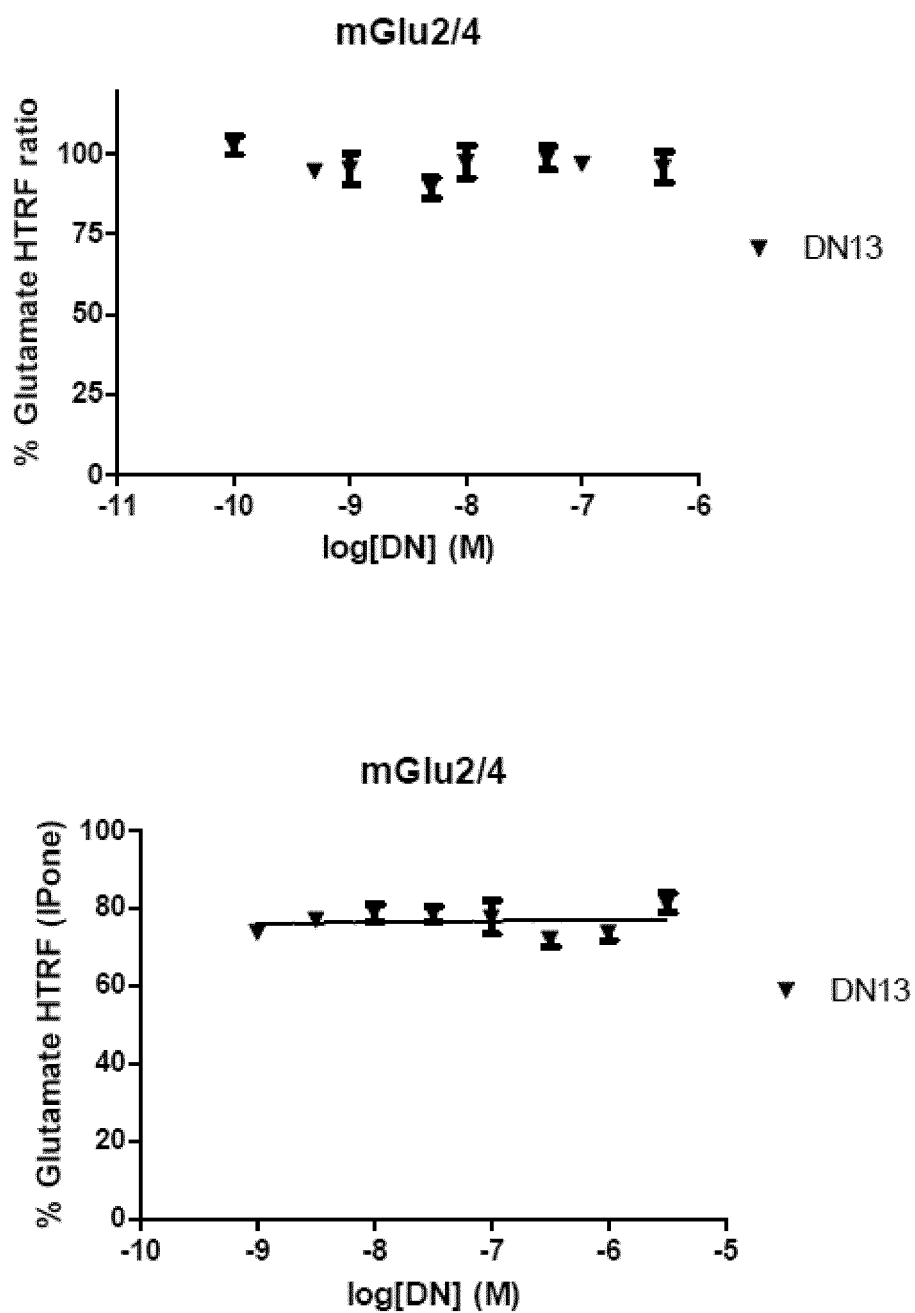

FIG. 6: DN13 does not activate the mGlu2-4 heterodimer. Top panel shows the absence of effect of DN13 on a mGlu2-4 heterodimer biosensor, in which the mGlu2 subunit is labeled on its Snap domain fused to the N terminus, while the mGlu4 subunit carries a Clip labeling domain. Bottom panel shows the absence of effect in G protein signaling, using a combination of mGlu2 and mGlu4 subunits that can reach the cell surface only when they are heterodimerized, using the control system developed based on the GABAB quality control system (Brock et al., J Biol Chem 2007)

Figure 7:
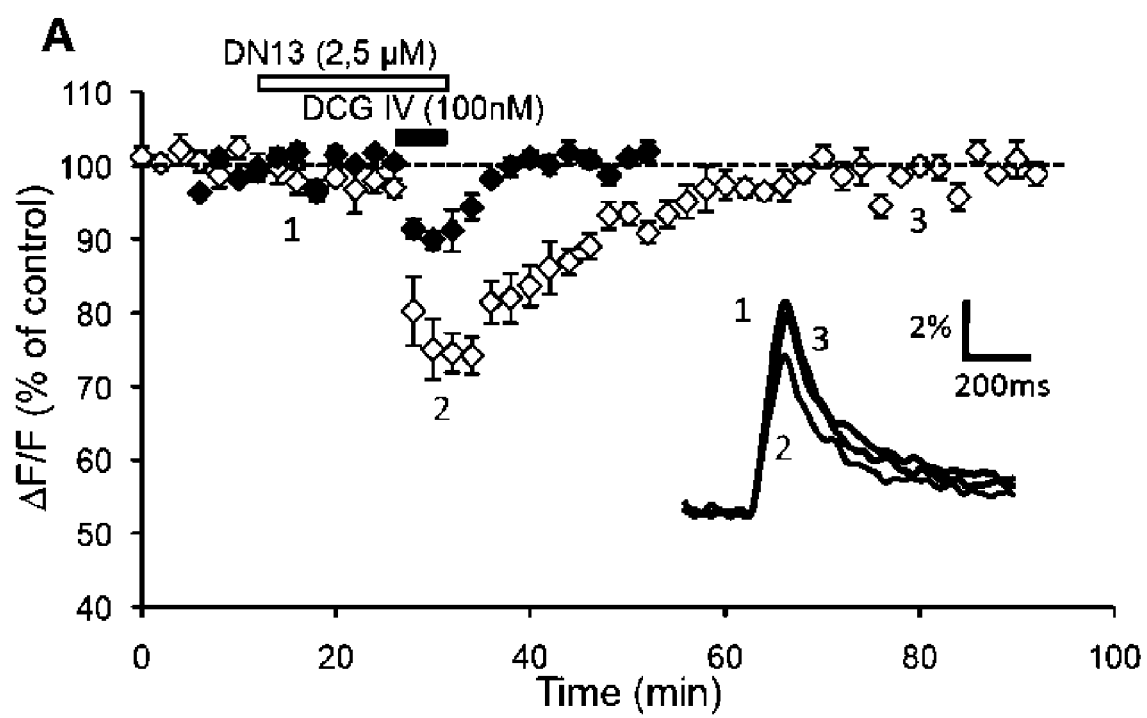

FIG. 7: Positive allosteric effect of DN13 at mossy fiber terminals in the CA3 area of the hippocampus. Ca signals were measured in the mossy fiber terminals upon electrical stimulation. The mGlu2-mGlu3 agonist DCG-IV, applied at low concentration induced a small decrease in the stimulation-induced increase in Ca signal. DN13 applied alone has no effect, but largely potentiated the effect of DCG-IV.

Figure 8:
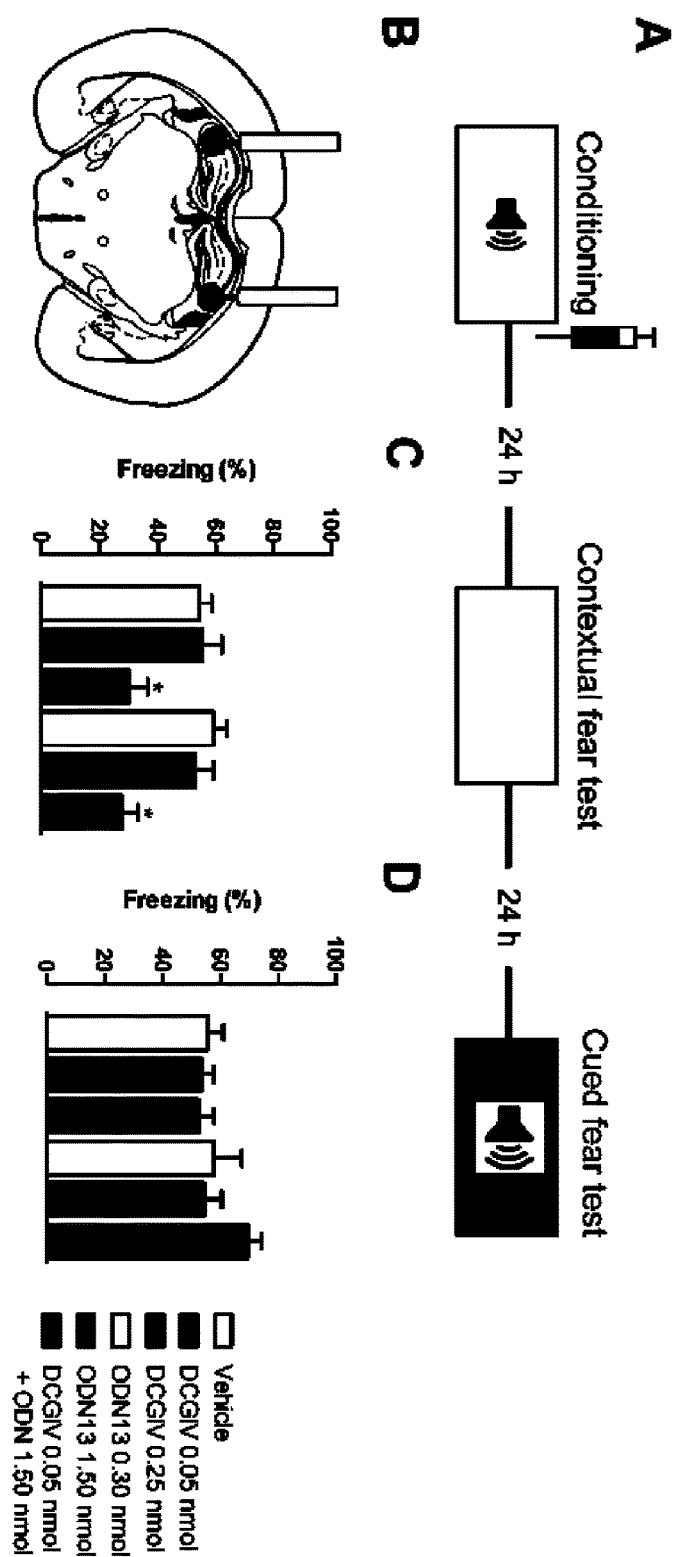

FIG. 8: DN13 potentiates the inhibition of contextual fear memory in living mice. Mice were implanted with canula in both CA3 area of the hippocampus, and then trained in a specific environment (context and sound) were they receive a small electric shock. They then received an injection of the indicated drugs, and tested for a fear response (freezing behavior) the day after. Low dose of the mGlu2-mGlu3 agonist DCG-IV did not inhibit the contextual fear, while higher dose did. DN13 had no effect. However, the co-injection of the low dose of DCG-IV and DN13 decreased the fear behavior, as did the high dose of DCG-IV. No effect was observed in response to the conditioning noise, as expected by the fact that the hippocampus is not involved in this type of memory.

Figure 9:
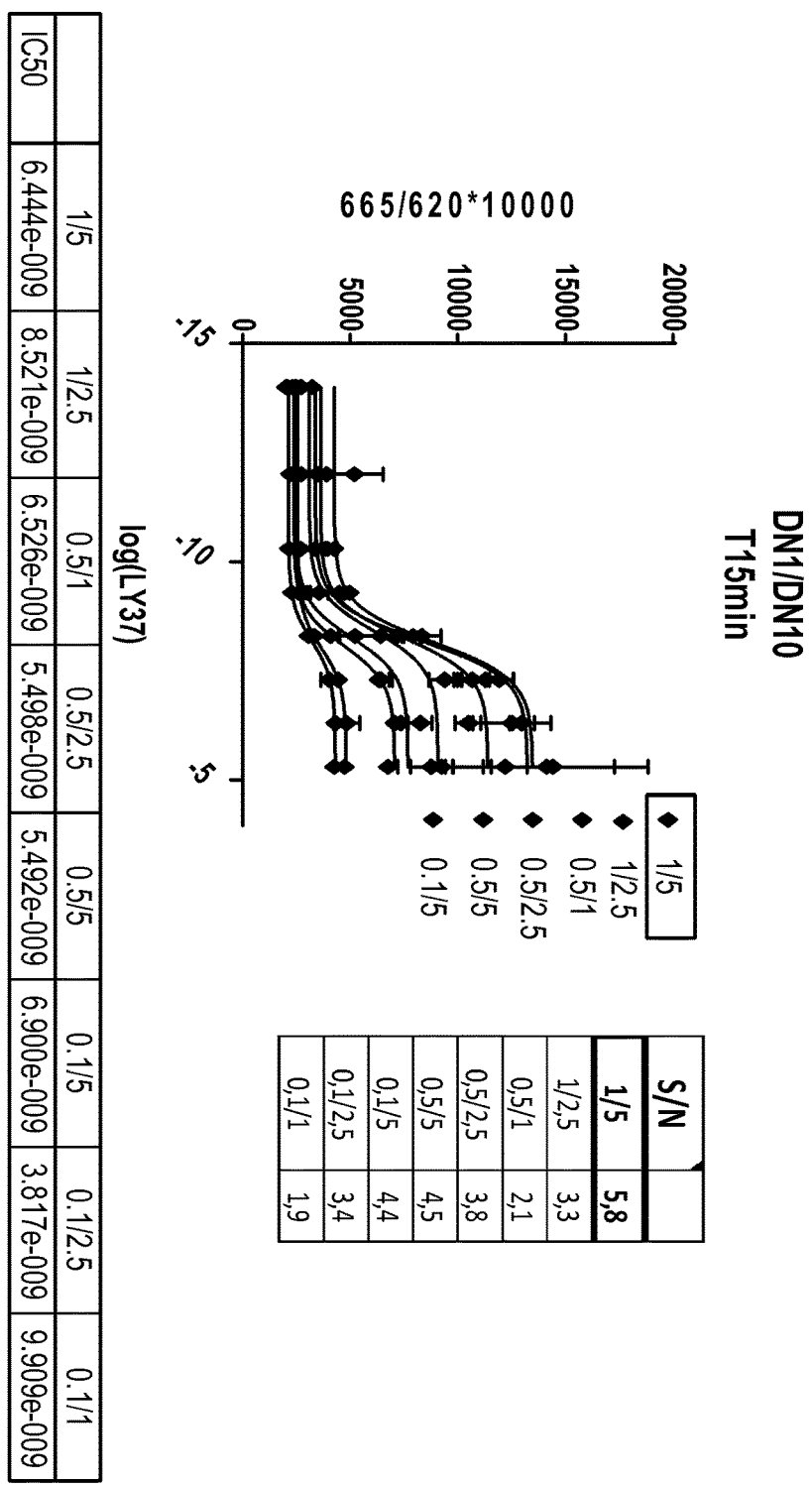

FIG. 9: Sensing mGlu2R activity using DN13. Data shows the increase in TR-FRET signals between an antibody recognizing mGlu2R labelled with Lumi4-Tb, and DN13 labeled with a TR-FRET acceptor, as a function of agonist concentration and the amount of DN13 used in the assay.

Figure 10A:
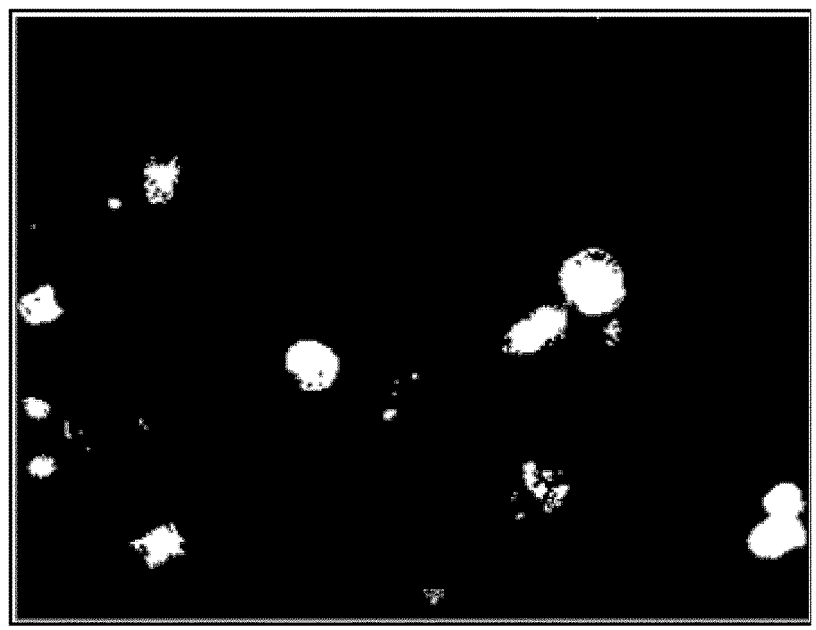
Figure 10A:
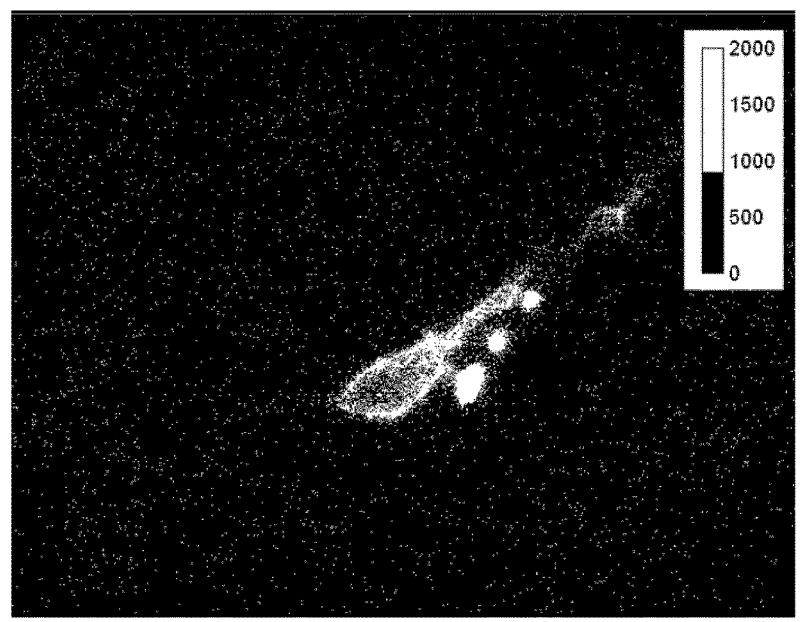
Figure 10B:
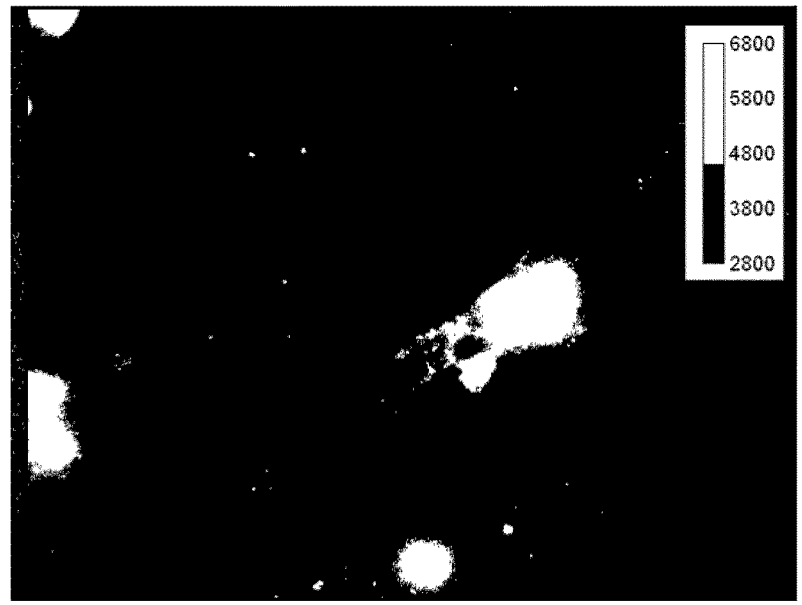
Figure 10B:
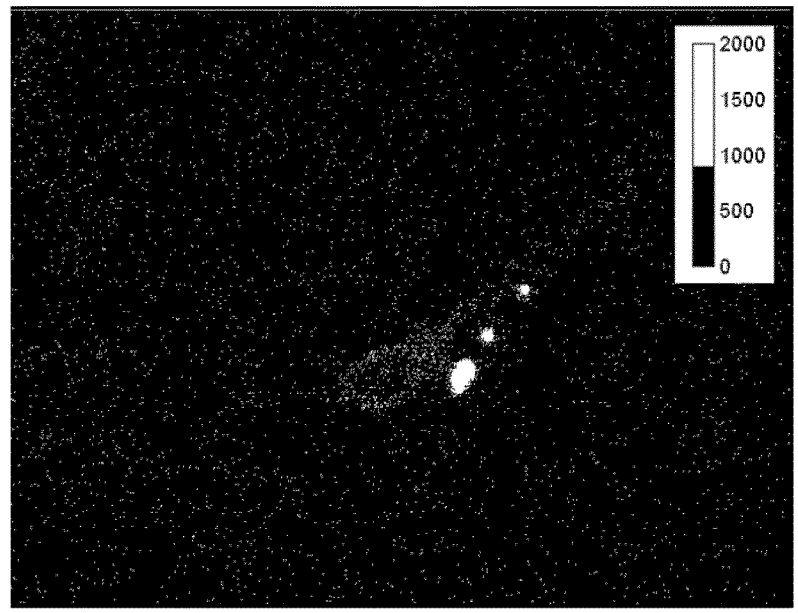

FIGS. 10A and B: Detecting active mGlu2R in primary neurons in culture. Hippocampal neurons were incubated with an antibody recognizing mGlu2R labelled with Lumi4-Tb, DN13 labeled with a TR-FRET acceptor, and the mGlu2R agonist. Note that the active form of mGlu2R can be detected by a FRET signal. No such signal could be measured in the presence of an mGlu2R antagonist.

EXAMPLE

Material & Methods

Llama Immunization and Library Construction

Two llamas (Lama glama) were immunized subcutaneously 4 times with $5\times10^7$ HEK293T cells transfected with rat mGluR2 and human mGluR2. VHH library constructions were performed in E.coli TG1 strain as previously described in Behar G, et al. (2009) Llama single-domain antibodies directed against nonconventional epitopes of tumor-associated carcinoembryonic antigen absent from nonspecific cross-reacting antigen. FEBS J 276(14):3881-3893 and Alvarez-Rueda N, et al. (2007) Generation of llama single-domain antibodies against methotrexate, a prototypical hapten. Mol Immunol 44(7):1680-1690. (Alvarez-Rueda, Behar et al. 2007, Behar, Chames et al. 2009). Library diversities were above $10^8$ transformants.

Selection of Single Domain Antibodies by Phage Display

20 µL of the bacteria library was grown in 50 mL of 2YTAG (2YT/Ampicillin 100 µg/mL)/2% Glucose) at 37° C. with shaking (250 rpm) to an $OD_{600}$ between 0.5 to 0.7. Bacteria were infected by KM13 helper phage using a multiplicity of infection of 20, during 30 min at 37° C. without shaking. The culture was centrifuged for 15 min at 3000 g, and bacterial pellet was resuspended in 250 mL of 2YTA/kanamycine (50 µg/mL) for an overnight phage-sdAb production at 30° C. with shaking. The overnight culture was split in 10 vials and centrifuged for 20 min at 3000 g. Five mL of 80% PEG8000, 2.5 mM NaCl were added to the supernatant in a new clean vial and incubated for 1 h on ice to induce phage particle precipitation. The solution was centrifuged for 20 min at 3000 g at 4° C. and the phage-containing pellet were re-suspended in 1 mL of PBS. Another centrifugation step (2 min, 14000 g) was performed to eliminate bacterial contaminant and 200 µL of PEG8000 NaCl was added to supernatants in a new vial. After 30 min on ice and a last centrifugation (5 min, 14000 g), phage-containing pellet were re-suspended in 1 mL PBS to obtain a ready to used Phage-sdAb for selections.

To obtain mGluR2 specific clones, a first round of selection (S1) was performed on Maxisorp plates (Nunc, Maxisorp®) coated 24 h at 4° C. with purified human mGluR2 reconstitued in nanodiscs according to El Moustaine D, Granier S, Doumazane E, Scholler P, Rahmeh R, Bron P, Mouillac B, Baneres J L, Rondard P, Pin J P. "Distinct roles of metabotropic glutamate receptor dimerization in agonist activation and G-protein coupling." Proc Natl Acad Sci U S A. 2012 Oct. 2; 109(40):16342-7. Before selection on purified mGluR2, phage-sdAb library was depleted by incubation with empty nanodisc (without receptor) to eliminate anti-nanodisc antibodies and to reduce non-specific binding. Remaining Phages and purified mGluR2 coated wells were saturated with 2% milk/PBS during 1 h at 4° C., and then phages and antigen were incubated together during 2 h at 4° C. for selection with shaking. Wells were washed 10 times with PBS. Bound phages were eluted by 1 mg/mL Trypsine solution (Sigma) during 30 min at room temperature with shaking. Phages were rescued and reamplified by infection of TG1 and phage production as above, yielding S1 polyclonal phage population.

To avoid non-specific selection against proteins that composed nanodics and to select antibodies against mGlu2 receptor in a cellular context, a second round of selection (S2) was performed on HEK293T cells transfected with rat mGluR2 ($2\times10^7$ cells). S1 polyclonal phage population and cells were saturated in 2% milk/PBS during 1 h at 4° C., and incubated together in same condition than described previously. After 5 PBS washes, bound phages were eluted using trypsin solution (1 mg/mL) during 30 min at room temperature. Phages were rescued in TG1 and infected bacteria corresponding to S2 were plated. Individual TG1 colonies from S2 were picked and grown in two different 96-deep-well plates in 400 µL of 2YTAG. After overnight growth, half of the culture was frozen at -80° C. in 20% glycerol for backup, and the rest of culture was used for soluble sdAb production induced by isopropyl-β-D-thiogalactopyranoside (IPTG). SdAb concentrations in supernatant were estimated at 100-500 nM using the DoubleTag check kit (Cisbio Bioassays).

Production and Purification of sdAb

For large scale sdAb production, positive phagemids from screening step were transformed in E.Coli BL21DE3 strain. Transformed bacteria were grown in 400 mL of 2YTA until 0D600=0.7 and induced with 100 µM IPTG for an overnight growth at 30° C. with shaking. The bacteria were pelleted and lysed by freeze-thawing and Bugbuster™ Protein Extraction Reagent (Novagen). After Centrifugation step (3000 g, 20 min), sdAbs were purified from the supernatant using metal affinity chromatography TALON® Superflow™ (GE Healthcare) according to the manufacturer's instructions (Even-Desrumeaux, Baty et al. 2010).

Time Resolved Fluorescence Resonance Energy Transfer (TR-FRET) Assays

HTRF® (Homogenous Time Resolved Fluorescence) combines standard FRET technology with time-resolved measurement of fluorescence (TR-FRET), allowing elimination of short-lived background fluorescence. In this study, HTRF assays were used for binding and competition experiments. Experiments were performed either on black 96 well plates or on white 384sv wells plates (Corning) and read on a PHERAstar FS (BMG LabTech).

Binding assays were performed using HEK-293 cells transfected with mGluR2-ST and HT receptors. After a 24 h transfection with Lipofectamine 2000 (Invitrogen) following the constructor's recommendation, adherent cells were washed with pre-warmed TagLite buffer. Cells were incubated with 100 nM SNAP-Tb (Donor fluorochrome from Cisbio Biossays) for 1 h at 37° C. During this step, Tb cryptate fluorochrome was covalently coupled to mGluR2 receptors via the SNAPTag fusion. Cells were washed 4 times directly on flasks using TagLite buffer, and were detached from their support using Accutase solution (Thermo). After 2 final TagLite washes, 10 µL of mGluR2-ST-Tb cells were dispensed on small volume wells with 5000 or 10000 cells/well. SdAbs were incubated with transfected cells and revealed generally by 200 nM of anti-His-D2 or anti-cMyc-D2. When using labeled sdAb-d2, anti-His-d2 was replaced by 5 µL of Taglite buffer. After 2 h incubation at 4° C., d2 acceptor TR-FRET signal (665 nm) and Tb donor signal (620 nm) were measured using a 50 µs delay, and a 450 µs integration upon excitation at 337 nm (on PHERAstar FS BMG LabTech). HTRF ratio (665 nm/620 nm$\times10^4$, Cisbio patent U.S. Pat. No. 5,527,684) was calculated for preventing interference due to medium variability, chemical compound or to normalize experiments when using cells expressing different receptors levels.

Measurement of IP accumulation in HEK293 cells transiently expressing mGluR2 after a 24h transfection with Lipofectamine 2000 (Invitrogen) was determined using the IP-One HTRF kit (CisBio Bioassays) according to the manufacturer's recommendations.

Datas from HTRF experiments were analyzed by Graph-Pad.

Reagents, Cell Lines and Antibodies

HEK293T cells were obtained from ATCC. Cells lines were cultivated in DMEM (Invitrogen) complemented with 10% (v/v) Bovine Serum gold (PAA). All drugs (LY341495, DCG-IV, LY354740) were from Tocris Bioscience. All HTRF Reagents, labeled Antibodies, labeled ligand, SNAP-tag Plasmids, were a kind Gift from Cisbio Bioassays.

Results

Anti-mGluR2 sdAbs were isolated from the repertoire of immunized llamas by alternating phages display selections on purified mGluR2 reconstituted in nanodiscs and on HEK 293T transfected with mGluR2. Three clones DN7, DN10 and DN13 representative of the final outputs and displaying different sequences were chosen, produced and purified for further characterization. Their binding on all mGluR2 family members was assayed by Homogenous-Time Resolved Fluorescence (HTRF) on transfected cells to confirm their specificity and their selectivity toward the other mGluR (FIG. 1). FIG. 2 shows that the single domain antibodies are specific for the active conformation of mGlu2R. Finally, the single domain antibodies activate mGlu2 in HEK293 transfected cells (FIG. 3) and prevent the dissociation of the agonist in rat hippocampal slices (FIG. 4A and B). DN13 is a positive allosteric modulator of mGlu2R (FIG. 5) and does not activate the mGlur2-4 heterodimer (FIG. 6), this provides additional information that nanobodies can be specific for a given composition subunit mGluR. FIG. 7 clearly shows that DN13 may increase the response of a low dose of agonist in the hippocampal slices. DN13 potentiates the inhibition of contextual fear memory in living mice (FIG. 8). FIG. 9 shows that nanobodies recognize only the active form, enabling the development of biosensors with a very good signal/noise ratio and unmodified recipient. FIG. 10 A and B show that it is possible to detect active mGlur2 in primary neurons in culture.

REFERENCES

Throughout this application, various references describe the state of the art to which this invention pertains. The disclosures of these references are hereby incorporated by reference into the present disclosure.

Alvarez-Rueda, N., G. Behar, V. Ferre, M. Pugniere, F. Roquet, L. Gastinel, C. Jacquot, J. Aubry, D. Baty, J. Barbet and S. Birkle (2007). "Generation of llama single-domain antibodies against methotrexate, a prototypical hapten." Mol Immunol 44(7): 1680-1690.

Behar, G., P. Chames, I. Teulon, A. Cornillon, F. Alshoukr, F. Roquet, M. Pugniere, J. L. Teillaud, A. Gruaz-Guyon, A. Pelegrin and D. Baty (2009). "Llama single-domain antibodies directed against nonconventional epitopes of tumor-associated carcinoembryonic antigen absent from nonspecific cross-reacting antigen." FEBS J 276(14): 3881-3893.

El Moustaine, D., S. Granier, E. Doumazane, P. Scholler, R. Rahmeh, P. Bron, B. Mouillac, J. L. Baneres, P. Rondard and J. P. Pin (2012). "Distinct roles of metabotropic glutamate receptor dimerization in agonist activation and G-protein coupling." Proc Natl Acad Sci USA 109(40): 16342-16347.

Even-Desrumeaux, K., D. Baty and P. Chames (2010). "Strong and oriented immobilization of single domain antibodies from crude bacterial lysates for high-throughput compatible cost-effective antibody array generation." Mol Biosyst 6(11): 2241-2248.

The invention claimed is:

1. An isolated single domain antibody comprising:
   i) a CDR1 having a sequence set forth as SEQ ID NO: 1, a CDR2 having a sequence set forth as SEQ ID NO: 2, and a CDR3 having a sequence set forth as SEQ ID NO: 3; or
   ii) a CDR1 having a sequence set forth as SEQ ID NO: 5, a CDR2 having a sequence set forth as SEQ ID NO: 6, and a CDR3 having a sequence set forth as SEQ ID NO: 7; or
   iii) a CDR1 having a sequence set forth as SEQ ID NO: 9, a CDR2 having a sequence set forth as SEQ ID NO: 10, and a CDR3 having a sequence set forth as SEQ ID NO: 11;
   wherein said isolated single domain antibody specifically binds metabotropic glutamate receptor 2 (mGluR2).

2. The isolated single domain antibody of claim 1 which has a sequence set forth as SEQ ID NO:4, SEQ ID NO:8 or SEQ ID NO:12.

3. The single domain antibody according to claim 1 which is a humanized single domain antibody.

4. A pharmaceutical composition comprising a single domain antibody according to claim 1 or a polypeptide comprising the single domain antibody.

5. The single domain antibody according to claim 1 or a polypeptide comprising the single domain antibody which is conjugated with a detectable label.

6. The single domain antibody or polypeptide of claim 5 wherein the detectable label is selected from the group consisting of radioisotope labels, fluorescent labels, chemiluminescent labels, enzyme labels, and bio luminescent labels.

7. A polypeptide comprising at least one single domain antibody comprising:
   i) a CDR1 having a sequence set forth as SEQ ID NO: 1, a CDR2 having a sequence set forth as SEQ ID NO: 2, and a CDR3 having a sequence set forth as SEQ ID NO: 3; or
   ii) a CDR1 having a sequence set forth as SEQ ID NO: 5, a CDR2 having a sequence set forth as SEQ ID NO: 6, and a CDR3 having a sequence set forth as SEQ ID NO: 7; or
   iii) a CDR1 having a sequence set forth as SEQ ID NO: 9, a CDR2 having a sequence set forth as SEQ ID NO: 10, and a CDR3 having a sequence set forth as SEQ ID NO: 11;
   and at least one further binding domain, wherein said single domain antibody specifically binds metabotropic glutamate receptor 2 (mGluR2).

8. The polypeptide of claim 7 wherein the at least one further binding domain is a single domain antibody.

9. The polypeptide of claim 7, wherein said polypeptide is a bispecific polypeptide.

10. The polypeptide of claim 7 wherein the at least one further binding domain is directed against transferrin.

11. The polypeptide of claim 7 which is a biparatopic polypeptide.

12. A polypeptide comprising a single domain antibody comprising:
   i) a CDR1 having a sequence set forth as SEQ ID NO: 1, a CDR2 having a sequence set forth as SEQ ID NO: 2, and a CDR3 having a sequence set forth as SEQ ID NO: 3; or
   ii) a CDR1 having a sequence set forth as SEQ ID NO: 5, a CDR2 having a sequence set forth as SEQ ID NO: 6, and a CDR3 having a sequence set forth as SEQ ID NO: 7; or
   iii) a CDR1 having a sequence set forth as SEQ ID NO: 9, a CDR2 having a sequence set forth as SEQ ID NO: 10, and a CDR3 having a sequence set forth as SEQ ID NO: 11;
   wherein the single domain antibody is linked to an immunoglobulin domain, and said single domain antibody specifically binds metabotropic glutamate receptor 2 (mGluR2).

13. The polypeptide of claim 12 wherein the immunoglobulin domain is a Fc portion.

14. A polypeptide comprising a first fusion protein wherein a CL constant domain of an antibody is fused by its N-terminal end to a C-terminal end of a single domain antibody, wherein said single domain antibody specifically binds metabotropic glutamate receptor 2 (mGluR2), comprising:
   i) a CDR1 having a sequence set forth as SEQ ID NO: 1, a CDR2 having a sequence set forth as SEQ ID NO: 2, and a CDR3 having a sequence set forth as SEQ ID NO:3; or
   ii) a CDR1 having a sequence set forth as SEQ ID NO: 5, a CDR2 having a sequence set forth as SEQ ID NO: 6, and a CDR3 having a sequence set forth as SEQ ID NO: 7; or
   iii) a CDR1 having a sequence set forth as SEQ ID NO: 9, a CDR2 having a sequence set forth as SEQ ID NO: 10, and a CDR3 having a sequence set forth as SEQ ID NO: 11;

and a second fusion protein wherein a CH1 constant domain of an antibody is fused by its N-terminal end to a C-terminal end of a single domain antibody directed against an antigen different from mGluR2.

15. A nucleic acid encoding
   a single domain antibody according to claim 1 or a polypeptide comprising the single domain antibody.

16. A vector which comprises the nucleic acid of claim 15.

17. A host cell which is transformed with the nucleic acid sequence of claim 15 or with a vector comprising the nucleic acid sequence.

18. A method of detecting activation of mGluR2 in a sample comprising the steps of
   i) contacting the sample with a single domain antibody of claim 1 or a polypeptide comprising the single domain antibody and,
   ii) detecting binding of said single domain antibody or said polypeptide to said sample wherein detection of binding is indicative of the activation of mGluR2.

* * * * *

UNITED STATES PATENT AND TRADEMARK OFFICE
CERTIFICATE OF CORRECTION

PATENT NO. : 10,174,115 B2
APPLICATION NO. : 15/323607
DATED : January 8, 2019
INVENTOR(S) : D. Baty et al.

It is certified that error appears in the above-identified patent and that said Letters Patent is hereby corrected as shown below:

On the Title Page

Item (73) UNIVERSITÉ DE VERSAILLES SAINT-QUENTIN-EN-YVELINES of Versailles, FRANCE should be identified as the eighth assignee.

Signed and Sealed this
Fourth Day of February, 2020

Andrei Iancu
*Director of the United States Patent and Trademark Office*

SEQUENCE LISTING

```
<160> NUMBER OF SEQ ID NOS: 18

<210> SEQ ID NO 1
<211> LENGTH: 8
<212> TYPE: PRT
<213> ORGANISM: Artificial
<220> FEATURE:
<223> OTHER INFORMATION: Synthetic DN7 CDR1

<400> SEQUENCE: 1

Gly Arg Thr Phe Arg Pro Tyr Gly
1               5

<210> SEQ ID NO 2
<211> LENGTH: 8
<212> TYPE: PRT
<213> ORGANISM: Artificial
<220> FEATURE:
<223> OTHER INFORMATION: Synthetic DN7 CDR2

<400> SEQUENCE: 2

Ile Ile Trp Ser Leu Gly Tyr Thr
1               5

<210> SEQ ID NO 3
<211> LENGTH: 12
<212> TYPE: PRT
<213> ORGANISM: Artificial
<220> FEATURE:
```

<223> OTHER INFORMATION: Synthetic DN7 CDR3

<400> SEQUENCE: 3

Ala Ala Arg Asp Arg Ser Ser Ser Glu Tyr Asp Tyr
1               5                   10

<210> SEQ ID NO 4
<211> LENGTH: 119
<212> TYPE: PRT
<213> ORGANISM: Artificial
<220> FEATURE:
<223> OTHER INFORMATION: Synthetic DN7 single domain antibody

<400> SEQUENCE: 4

Gln Val Gln Leu Val Gln Ser Gly Gly Gly Tyr Val Gln Ala Gly Gly
1               5                   10                  15

Ser Leu Ser Val Ser Cys Ala Ala Ser Gly Arg Thr Phe Arg Pro Tyr
            20                  25                  30

Gly Val Gly Trp Phe Arg Gln Ala Pro Gly Lys Glu Arg Glu Phe Val
        35                  40                  45

Ala Ala Ile Ile Trp Ser Leu Gly Tyr Thr Ile Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ala Glu Asp Thr Ala Val Tyr Tyr Cys
                85                  90                  95

Ala Ala Arg Asp Arg Ser Ser Ser Glu Tyr Asp Tyr Trp Gly Gln Gly
            100                 105                 110

Thr Gln Val Thr Val Ser Ser
        115

<210> SEQ ID NO 5
<211> LENGTH: 8
<212> TYPE: PRT
<213> ORGANISM: Artificial
<220> FEATURE:
<223> OTHER INFORMATION: Synthetic DN10 CDR1

<400> SEQUENCE: 5

Gly Arg Thr Asp Ser Ile Tyr Ser
1               5

<210> SEQ ID NO 6
<211> LENGTH: 8
<212> TYPE: PRT
<213> ORGANISM: Artificial
<220> FEATURE:
<223> OTHER INFORMATION: Synthetic DN10 CDR2

<400> SEQUENCE: 6

Ile Thr Trp Arg Arg Glu Tyr Thr
1               5

<210> SEQ ID NO 7
<211> LENGTH: 12
<212> TYPE: PRT
<213> ORGANISM: Artificial
<220> FEATURE:
<223> OTHER INFORMATION: Synthetic DN10 CDR3

<400> SEQUENCE: 7

Ala Leu Arg Pro Gly Leu Arg Asp Asp Leu Asn Tyr
1               5                   10

<210> SEQ ID NO 8
<211> LENGTH: 119
<212> TYPE: PRT
<213> ORGANISM: Artificial
<220> FEATURE:
<223> OTHER INFORMATION: Synthetic DN10 single domain antibody

<400> SEQUENCE: 8

Glu Val Gln Leu Val Glu Ser Gly Gly Val Val Gln Pro Gly Asp
1               5                   10                  15

Ser Leu Arg Leu Ser Cys Val Ala Ser Gly Arg Thr Asp Ser Ile Tyr
            20                  25                  30

Ser Met Ala Trp Phe Arg Gln Ala Pro Gly Lys Glu Arg Glu Phe Val
        35                  40                  45

Ala Ile Ile Thr Trp Arg Glu Tyr Thr Asn Tyr Glu Asp Ser Val
    50                  55                  60

Arg Gly Arg Phe Thr Ile Ser Arg Asp Asn Ala Lys Asn Ala Val Tyr
65                  70                  75                  80

Leu Gln Met Asn Lys Leu Lys Pro Glu Asp Thr Ala Val Tyr Tyr Cys
                85                  90                  95

Ala Leu Arg Pro Gly Leu Arg Asp Asp Leu Asn Tyr Trp Gly Gln Gly
            100                 105                 110

Thr Gln Val Thr Val Ser Ser
        115

<210> SEQ ID NO 9
<211> LENGTH: 8
<212> TYPE: PRT
<213> ORGANISM: Artificial
<220> FEATURE:
<223> OTHER INFORMATION: Synthetic DN13 CDR1

<400> SEQUENCE: 9

Val Arg Phe Phe Ser Ile Asn Thr
1               5

<210> SEQ ID NO 10
<211> LENGTH: 7
<212> TYPE: PRT
<213> ORGANISM: Artificial
<220> FEATURE:
<223> OTHER INFORMATION: Synthetic DN13 CDR2

<400> SEQUENCE: 10

Ile Thr Ser Ser Gly Ser Thr
1               5

<210> SEQ ID NO 11
<211> LENGTH: 12
<212> TYPE: PRT
<213> ORGANISM: Artificial
<220> FEATURE:
<223> OTHER INFORMATION: Synthetic DN13 CDR3

<400> SEQUENCE: 11

His Ala Asp Tyr Lys Tyr Thr Thr His Asn Thr Ala
1               5                   10

<210> SEQ ID NO 12
<211> LENGTH: 118
<212> TYPE: PRT
<213> ORGANISM: Artificial

<220> FEATURE:
<223> OTHER INFORMATION: Synthetic DN13 single domain antibody

<400> SEQUENCE: 12

Gln Val Gln Leu Val Gln Ser Gly Gly Gly Leu Val Gln Ala Gly Gly
1               5                   10                  15

Ser Leu Arg Leu Ser Cys Ala Ala Ser Val Arg Phe Phe Ser Ile Asn
            20                  25                  30

Thr Met Gly Trp Tyr Arg Gln Ala Pro Gly Lys Gln Arg Glu Leu Val
        35                  40                  45

Ala Asp Ile Thr Ser Ser Gly Ser Thr Asn Tyr Ala Asp Ser Gly Lys
    50                  55                  60

Gly Arg Phe Thr Ile Ser Arg Asp Asn Ala Lys Asn Thr Val Tyr Leu
65                  70                  75                  80

Gln Met Asn Arg Leu Lys Pro Glu Asp Thr Ala Val Tyr Tyr Cys His
                85                  90                  95

Ala Asp Tyr Lys Tyr Thr Thr His Asn Thr Ala Trp Gly Gln Gly Thr
            100                 105                 110

Gln Val Thr Val Ser Ser
        115

<210> SEQ ID NO 13
<211> LENGTH: 15
<212> TYPE: PRT
<213> ORGANISM: Artificial
<220> FEATURE:
<223> OTHER INFORMATION: Synthetic linker

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 20
<212> TYPE: PRT
<213> ORGANISM: Artificial
<220> FEATURE:
<223> OTHER INFORMATION: Synthetic linker

<400> SEQUENCE: 14

Gly Gly Gly Gly Ser Gly Gly Gly Gly Ser Gly Gly Gly Gly Ser Gly
1               5                   10                  15

Gly Gly Gly Ser
            20

<210> SEQ ID NO 15
<211> LENGTH: 5
<212> TYPE: PRT
<213> ORGANISM: Artificial
<220> FEATURE:
<223> OTHER INFORMATION: Synthetic linker

<400> SEQUENCE: 15

Gly Gly Gly Gly Ser
1               5

<210> SEQ ID NO 16
<211> LENGTH: 3
<212> TYPE: PRT
<213> ORGANISM: Artificial
<220> FEATURE:
<223> OTHER INFORMATION: Synthetic linker

```
<400> SEQUENCE: 16

Gly Gly Ser
1

<210> SEQ ID NO 17
<211> LENGTH: 3
<212> TYPE: PRT
<213> ORGANISM: Artificial
<220> FEATURE:
<223> OTHER INFORMATION: Synthetic linker

<400> SEQUENCE: 17

Gly Gly Gly
1

<210> SEQ ID NO 18
<211> LENGTH: 15
<212> TYPE: PRT
<213> ORGANISM: Artificial
<220> FEATURE:
<223> OTHER INFORMATION: Synthetic linker

<400> SEQUENCE: 18

Gly Gly Gly Ser Ser Gly Gly Gly Ser Ser Gly Gly Gly Ser Ser
1               5                   10                  15
```